(12) United States Patent
Hammon et al.

(10) Patent No.: US 7,115,776 B2
(45) Date of Patent: Oct. 3, 2006

(54) HETEROGENEOUSLY CATALYZED GAS-PHASE PARTIAL OXIDATION OF AT LEAST ONE ORGANIC COMPOUND

(75) Inventors: Ulrich Hammon, Mannheim (DE); Jochen Petzoldt, Mannheim (DE); Klaus Joachim Müller-Engel, Stutensee (DE); Martin Dieterle, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 495 days.

(21) Appl. No.: 10/460,153

(22) Filed: Jun. 13, 2003

(65) Prior Publication Data

US 2004/0015013 A1 Jan. 22, 2004

(30) Foreign Application Priority Data

Jul. 18, 2002 (DE) ................. 102 32 748

(51) Int. Cl.
*C07C 51/16* (2006.01)
(52) U.S. Cl. .................................... 562/547
(58) Field of Classification Search .............. None
See application file for complete search history.

(56) References Cited

U.S. PATENT DOCUMENTS

| | | | |
|---|---|---|---|
| 3,119,837 A | 1/1964 | Kingsley et al. | |
| 3,702,259 A | 11/1972 | Nielsen | |
| 3,799,886 A | 3/1974 | Felice et al. | |
| 3,956,377 A | 5/1976 | Dolhyj et al. | |
| 4,077,912 A | 3/1978 | Dolhyj et al. | |
| 4,408,079 A | 10/1983 | Merger et al. | |
| 4,496,770 A | 1/1985 | Duembgen et al. | |
| 5,144,091 A | 9/1992 | Martan et al. | |
| 5,221,767 A | 6/1993 | Boehning et al. | |
| 5,231,226 A | 7/1993 | Hammon et al. | |
| 5,264,625 A | 11/1993 | Hammon et al. | |
| 5,442,108 A | 8/1995 | Kawajiri et al. | |
| 5,462,652 A | 10/1995 | Wegerer | |
| 5,668,077 A | 9/1997 | Klopries et al. | |
| 5,739,391 A | 4/1998 | Ruppel et al. | |
| 5,821,390 A | 10/1998 | Ruppel et al. | |
| 6,090,977 A | 7/2000 | Hefner et al. | |
| 6,252,122 B1 | 6/2001 | Tenten et al. | |
| 6,395,936 B1 | 5/2002 | Arnold et al. | |
| 6,403,829 B1 | 6/2002 | Unverricht et al. | |
| 6,525,217 B1 * | 2/2003 | Unverricht et al. | 562/544 |
| 2003/0017095 A1 * | 1/2003 | Olbert et al. | 422/196 |

FOREIGN PATENT DOCUMENTS

| | | |
|---|---|---|
| DE | 1 254 137 | 11/1967 |
| DE | 2 025 430 | 12/1971 |
| DE | 2 159 346 | 6/1972 |
| DE | 2 106 796 | 8/1972 |
| DE | 2 351 151 | 4/1974 |
| DE | 25 26 238 | 1/1976 |
| DE | 40 22 212 | 1/1992 |
| DE | 41 32 263 | 4/1993 |
| DE | 41 32 684 | 4/1993 |
| DE | 43 11 608 | 12/1994 |
| DE | 44 31 949 | 3/1995 |
| DE | 44 31 957 | 3/1995 |
| DE | 196 22 331 | 12/1997 |
| DE | 198 36 792 | 2/2000 |
| DE | 199 10 506 | 9/2000 |
| DE | 199 10 508 | 9/2000 |
| DE | 199 27 624 | 12/2000 |
| DE | 199 48 241 | 4/2001 |
| DE | 199 48 248 | 4/2001 |
| DE | 199 48 523 | 4/2001 |
| DE | 199 55 168 | 5/2001 |
| DE | 100 24 348 | 11/2001 |
| DE | 100 28 582 | 12/2001 |
| DE | 100 32 304 | 1/2002 |
| DE | 101 34 026 | 1/2002 |
| DE | 100 46 672 | 3/2002 |
| DE | 100 46 957 | 4/2002 |
| DE | 101 21 592 | 5/2002 |
| DE | 101 01 695 | 7/2002 |
| DE | 101 37 768 | 9/2002 |
| DE | 100 46 928 | 11/2002 |
| DE | 102 32 967 | 12/2002 |
| DE | 101 31 297 | 1/2003 |
| EP | 0 058 927 | 9/1982 |
| EP | 0 092 097 | 10/1983 |
| EP | 0 253 409 | 1/1988 |
| EP | 0 372 972 | 6/1990 |
| EP | 0 415 347 | 3/1991 |
| EP | 0 468 290 | 1/1992 |
| EP | 0 471 853 | 2/1992 |
| EP | 0 522 871 | 1/1993 |
| EP | 0 529 853 | 3/1993 |
| EP | 0 608 838 | 8/1994 |

(Continued)

OTHER PUBLICATIONS

H. Beyer, et al., Lehrbuch der Organishchen Chemie, vol. 17, p. 261, "Mehrwertige Alkohole", 1973.

*Primary Examiner*—Paul A. Zucker
(74) *Attorney, Agent, or Firm*—Oblon, Spivak, McClelland, Maier & Neustadt, P.C.

(57) ABSTRACT

A process for the heterogeneously catalyzed gas-phase partial oxidation of an organic compound over a fixed catalyst bed present in a fixed-bed reactor having a plurality of catalyst tubes, in which the reduction of the quality of the catalyst load with increasing duration of operation is restored by a partial catalyst change, is described.

39 Claims, No Drawings

FOREIGN PATENT DOCUMENTS

| | | |
|---|---|---|
| EP | 0 614 872 | 9/1994 |
| EP | 0 700 714 | 3/1996 |
| EP | 0 700 893 | 3/1996 |
| EP | 0 731 080 | 9/1996 |
| EP | 0 911 313 | 4/1999 |
| EP | 1 090 684 | 4/2001 |
| EP | 1 097 745 | 5/2001 |
| GB | 1 277 050 | 6/1972 |
| GB | 1 291 354 | 10/1972 |
| GB | 1 464 198 | 2/1977 |
| WO | WO 01/87476 | 11/2001 |
| WO | WO 01/63270 | 12/2001 |

\* cited by examiner

HETEROGENEOUSLY CATALYZED GAS-PHASE PARTIAL OXIDATION OF AT LEAST ONE ORGANIC COMPOUND

The present invention relates to a process for the heterogeneously catalyzed gas-phase partial oxidation of at least one organic compound with molecular oxygen over a fixed catalyst bed present in a fixed-bed reactor containing a plurality of catalyst tubes, in which there is an increasing reduction of the quality of the catalyst load with increasing duration of operation from a specific operating time.

Here, complete oxidation of an organic compound with molecular oxygen is understood as meaning that the organic compound is converted under the reactive action of molecular oxygen so that all the carbon contained in the organic compound is converted into oxides of carbon and all the hydrogen contained in the organic compound is converted into oxides of hydrogen. All those reactions of an organic compound under the reactive action of molecular oxygen which differ from these are summarized here as the partial oxidation of an organic compound.

In particular, partial oxidation is to be understood here as meaning those reactions of organic compounds under the reactive action of molecular oxygen in which the organic compound to be partially oxidized contains at least one chemically bonded oxygen atom more after the end of the reaction than before the partial oxidation was carried out.

It is generally known that numerous key chemicals can be produced by partial and heterogeneously catalyzed oxidation of various organic compounds with molecular oxygen in the gas phase. Examples are (cf. also EP-A 731080) the conversion of propylene to acrolein and/or acrylic acid (cf. for example DE-A 2351151), the conversion of tert-butanol, isobutene, isobutane, isobutyraldehyde or the methyl ether of tert-butanol to methacrolein and/or methacrylic acid (cf. for example DE-A 2526238, EP-A 92097, EP-A 58927, DE-A 4132263, DE-A 4132684 and DE-A 4022212), the conversion of acrolein to acrylic acid, the conversion of methacrolein to methacrylic acid (cf. for example DE-A 2526238), the conversion of o-xylene or naphthalene to phthalic anhydride (cf. for example EP-A 522871), the conversion of butadiene to maleic anhydride (cf. for example DE-A 2106796 and DE-A 1624921), the conversion of n-butane to maleic anhydride (cf. for example GB-A 1464198 and GB-A 1291354), the conversion of indanes to, for example, anthraquinone (cf. for example DE-A 2025430), the conversion of ethylene to ethylene oxide or propylene to propylene oxide (cf. for example DE-AS 1254137, DE-A 2159346, EP-A 372972, WO 89/0710, DE-A 4311608 and Beyer, Lehrbuch der organischen Chemie, 17th edition (1973), Hirzel Verlag Stuttgart, page 261), the conversion of propylene and/or acrolein to acrylonitrile (cf. for example DE-A 2351151), the conversion of isobutene and/or methacrolein to methacrylonitrile (i.e. the term partial oxidation here is also intended to include the term partial ammoxidation, i.e. a partial oxidation in the presence of ammonia), the oxidative dehydrogenation of hydrocarbons (cf. for example DE-A 2351151), the conversion of propane to acrylonitrile or to acrolein and/or acrylic acid (cf. for example DE-A 10131297, EP-A 1090684, EP-A 608838, DE-A 10046672, EP-A 529853, WO 01/96270 and DE-A 10028582) etc.

In order to ensure that the desired gas-phase partial oxidation takes place in preference to the complete oxidation, the former is usually carried out as a heterogeneously catalyzed oxidation over the surface of catalysts present in the solid state. Solid-state catalysts are frequently oxide materials or noble metals (e.g. Ag). The catalytically active oxide material may contain only one other element or more than one element (in the case of multielement oxide materials) apart from oxygen.

Particularly frequently used catalytically active oxide materials are those which comprise more than one metallic, in particular transition metal, element. In this case, the term multimetal oxide materials is used. Usually, multielement oxide materials are not simple physical mixtures of oxides of the elemental constituents but heterogeneous mixtures of complex polycompounds of these elements. In practice, the abovementioned catalytically active solid materials are as a rule molded to give a very wide range of geometries (rings, solid cylinders, spheres, etc.) before being used. The molding can be effected by molding the catalytically active material as such (for example in extruders) so that an unsupported catalyst results, or by applying the active material to a premolded support. Examples of catalysts which are suitable for heterogeneously catalyzed gas-phase partial oxidation are to be found, for example, in DE-A 10046957, EP-A 1097745, DE-A 4431957, DE-A 10046928, DE-A 19910506, DE-A 19622331, DE-A 10121592, EP-A 700714, DE-A 19910508, EP-A 415347, EP-A 471853 and EP-A 700893.

In general, heterogeneously catalyzed gas-phase partial oxidations are carried out at elevated temperatures (as a rule, a few hundred ° C., usually from 100 to 600° C.).

The operating pressure in heterogeneously catalyzed gas-phase partial oxidations may be below 1 atm, 1 atm or above 1 atm. As a rule, it is from 1 to 10 atm.

Since most heterogeneously catalyzed gas-phase partial oxidations are strongly exothermic, the sole measure of concomitantly using a catalyst is not sufficient for ensuring a very selective conversion of the organic compound to be oxidized to give the desired product, owing to a variety of possible simultaneous or subsequent reactions. Rather, the variation of the reaction temperature must additionally be controlled to a certain extent for carrying out selective heterogeneously catalyzed gas-phase partial oxidations in a controllable manner.

A generally used facility for controlling the liberated heat of reaction is to dilute the reactants molecular oxygen and organic compound to be partially oxidized with inert gases, such as $N_2$, oxides of carbon, such as $CO_2$ and CO, inert hydrocarbons, recycled reaction exit gases and/or steam, the use of diluent gases having a very high molar heat capacity being particularly advantageous (cf. EP-A 253409). The term inert means that preferred diluent gases are those which remain chemically unchanged in the course of the partial oxidation to an extent of at least 95 mol %, preferably at least 97 or 99 mol %. The feed gas mixture of a heterogeneously catalyzed gas-phase partial oxidation of at least one organic compound will therefore as a rule also comprise at least one inert diluent gas in addition to this organic compound and molecular oxygen.

A further generally used method for controlling the reaction temperature is to carry out the heterogeneously catalyzed gas-phase partial oxidation in a fixed-bed reactor containing a plurality of catalyst tubes. Such reactors correspond in their type to the shell-and-tube heat exchangers, i.e. their conventional design consists of a generally cylindrical container which houses a multiplicity of tubes (a tube bundle) corresponding to the cooling tubes of a shell-and-tube heat exchanger in a usually vertical arrangement. These catalyst tubes, each of which contains a fixed-bed arrangement of the corresponding catalyst load, are fixed with a seal at their ends in tube sheets and open into one hood each connected at the upper and lower end to the container. The reaction gas mixture flowing through the catalyst tube is fed in and removed above these hoods so that each catalyst tube corresponds to an elongated uniform reaction zone.

The chemical reaction takes place when the reaction gas mixture flows through the fixed bed during the residence time of the reaction gas mixture therein.

Furthermore, heat exchange media are passed through the space surrounding the catalyst tubes in order to cope with the process heat. After emerging from the container, the heat exchange media are brought back to their original temperature, for example in external heat exchangers, before they enter the reaction container again (cf. for example DE-A 30242468).

If the heat exchange medium enters the reactor along the catalyst tubes at different heights (a plurality of heights), this is referred to as using a plurality of heat exchange medium circulations or as a multizone reactor having a plurality of heating zones (the individual circulations are as a rule substantially separated from one another by suitable sheet metal partitions). If the heat exchange medium enters only at one height, this is referred to as a heat exchange medium circulation or as a one-zone reactor, even if this circulation is operated not with one pump but, for reasons of expediency, with a plurality of pumps.

Examples of such one-zone and multizone reactors are to be found, for example, in DE-A 10024348, DE-A 19836792, DE-A 10032304, WO 01/87476, DE-A 19910508, DE-A 19910506, DE-A 19927624, DE-A 19948241, DE-A 19948248, DE-A 19948523, DE-A 1995516, DE-A 10134026, DE-A 10101695, U.S. Pat. No. 5,442,108, EP-A 911313, EP-A 1097745, DE-A 10137768, DE-A 10135498 and DE-A 10040781.

Usually, the catalyst tubes are made of ferritic steel and frequently have a wall thickness of from 1 to 3 mm. Their internal diameter is often from 20 to 30 mm. The tube length is usually a few meters (a catalyst tube length of from 2 to 4 m is typical). It is expedient in terms of application technology if the number of catalyst tubes housed in the container is at least 5 000, preferably at least 10 000. Frequently, the number of catalyst tubes housed in the reaction container is from 15 000 to 30 000. Tube-bundle reactors having more than 40 000 catalyst tubes tend to be the exception. The catalyst tubes are usually homogeneously distributed inside the container, the distribution expediently being chosen so that the spacing between the central inner axes of adjacent catalyst tubes (i.e. the catalyst tube spacing) is from 30 to 50 mm, frequently from 35 to 45 mm (cf. for example EP-A 468290).

Particularly suitable heat exchange media are fluid heating media. It is frequently suitable to use salt melts, for example those of salts such as potassium nitrate, potassium nitrite, sodium nitrite and/or sodium nitrate. In some cases, however, melts of metals having a low melting point, such as sodium, mercury and alloys of various metals, are also used.

The heat exchange medium can be fed in a simple manner substantially directly longitudinally (cocurrent with or countercurrent to the reaction gas mixture) to the catalyst tubes. However, it is also possible for this longitudinal feed (cocurrent with or countercurrent to the reaction gas mixture) to be realized only when considered over the entire reaction container and to superpose on this longitudinal flow, inside the reaction container, a transverse flow by means of an arrangement of baffle plates which is present successively along the catalyst tubes, which baffle plates leave free passage cross-sections, so that a meander-like flow of the heat exchange medium results in the longitudinal section through the tube bundle. As a rule, the heat exchange medium leaves the reactor at a temperature which is above its inlet temperature. The above statements are valid in particular for heterogeneously catalyzed gas-phase partial oxidation of propylene to acrolein and/or acrylic acid, of isobutene to methacrolein and/or methacrylic acid, of (meth) acrolein to (meth)acrylic acid, of propane to acrolein and/or acrylic acid and of isobutane to methacrolein and/or methacrylic acid.

The disadvantage of processes for the heterogeneously catalyzed gas-phase partial oxidation of at least one organic compound of molecular oxygen over a fixed catalyst bed present in a fixed-bed reactor containing a plurality of catalyst tubes is that there is an increasing reduction of the quality of the catalyst load with increasing duration of operation from a specific operating time. This relates as a rule both to the catalyst activity (the higher the temperature required for specific conversion, the lower the activity) and to the selectivity of the formation of desired product.

It is also known that the reaction temperature generally passes through a certain maximum in the direction of flow of the reaction gas mixture along a catalyst tube (cf. for example DE-A 4431949), which in some cases greatly reduces the catalyst quality in this region as a function of time. The prior art makes a wide range of recommendations for overcoming said disadvantage. One proposal is to reduce the diameter of the catalyst tubes in order to increase the heat removal per unit volume of the catalyst. According to another proposed method, an attempt is made to suppress the formation of the maxima by varying the volume-specific activity of the catalytic load along the catalyst tubes (for example stepwise or continuously increasing in the direction of flow). An alternative possibility for reducing the formation of maxima is to reduce the loading of the reactor with reaction gas mixture or to allow the salt bath (heat exchange medium) to flow in a meandering manner in order to improve the heat removal. In some cases, a tube-bundle reactor having more than one temperature zone is also recommended, the temperature of the first zone in the direction of flow being chosen to be particularly low, as a rule lower than in the subsequent stages. However, said measures cannot prevent the quality of the entire catalyst load from decreasing per se with increasing duration of operation, even when the abovementioned measures for the formation of the maxima are applied.

The prior art attempts to counteract this fact by regenerating the catalyst load from time to time after certain durations of operation by passing over suitable regeneration gases containing molecular oxygen (cf. EP-A 614872). The disadvantage of this procedure, however, is that its efficiency is exhausted with increasing total duration of operation. Otherwise, the prior art counteracts the exhaustion of the quality of the catalyst load with increasing duration of operation by removing the entire catalyst load after a certain duration of operation from the fixed-bed reactor containing a plurality of catalyst tubes and replacing it with a fresh catalyst load.

The disadvantage of this procedure, however, is that the preparation of the required catalysts is comparatively complicated and expensive. As a rule, the costs for a complete catalyst load of an industrial fixed-bed reactor containing a plurality of catalyst tubes are in the region of seven figures.

It is an object of the present invention to provide an improved process for the heterogeneously catalyzed gas-phase partial oxidation of at least one organic compound with molecular oxygen over a fixed catalyst bed present in a fixed-bed reactor having a plurality of catalyst tubes, in which there is an increasing reduction of the quality of the catalyst load with increasing duration of operation from a specific operating time, which process takes into account the described catalyst exhaustion in a better manner than the prior art measures described.

We have found that this object is achieved by a process for the heterogeneously catalyzed gas-phase partial oxidation of at least one organic compound with molecular oxygen over a fixed catalyst bed present in a fixed-bed reactor having a plurality of catalyst tubes, in which there is an increasing reduction of the quality of the catalyst load with increasing duration of operation from a specific operating time, wherein, in order to recover the quality of the catalyst load, only a portion of the spent catalyst load, instead of the entire spent catalyst load, is removed from the fixed-bed reactor having a plurality of catalyst tubes and is replaced with a fresh catalyst load.

Surprisingly, the abovementioned measure results in a disproportionate restoration of the performance of the catalyst load even when measures were taken (for example the abovementioned ones, such as volume-specific activity of the catalyst load increasing stepwise or continuously in the direction of flow of the feed gas mixture along the catalyst tubes and/or meander-like flow of the heat exchange medium and/or two temperature zones, of which the first in the direction of flow of the reaction gas has a lower temperature than the second) which substantially suppress the formation of a maximum of the reaction temperature along the catalyst tube.

This is frequently due to the fact that, as a rule, either the feed gas mixture already contains small amounts of catalyst poisons because the industrial feed does not start from high-purity raw materials, or such catalyst poisons form only in the course of the partial oxidation carried out. Regarding such catalyst poisons, the fixed catalyst bed then in fact acts like an absorber in which the catalyst poison accumulates in an inhomogeneous manner along the load.

The novel procedure is as a rule therefore particularly advantageous in the second stage of a two-stage heterogeneously catalyzed gas-phase partial oxidation in which the product gas mixture from the first stage is used for feeding the fixed-bed reactor having a plurality of catalyst tubes in the second oxidation stage without intermediate purification, if necessary after addition of further molecular oxygen required for the oxidation of the second stage and, if required, additional inert gas. Of course, the abovementioned context is also applicable, in multistage heterogeneously catalyzed gas-phase partial oxidations, to any pair of preceding stage and subsequent stage.

A multistage heterogeneously catalyzed gas-phase partial oxidation is present when the entire oxidation process is carried out in a series of at least two oxidation reactors. It is used as a rule when (for example for reasons relating to heat removal) the conversion is to be distributed over a plurality of reactors or when a partial oxidation takes place in a plurality of successive steps and each step is carried out in a fixed-bed reactor intended for said step and containing a plurality of catalyst tubes, it being possible to adapt the reaction conditions and the catalyst load in an optimum manner to the respective step. Here too, the product gas mixture of the preceding stage is as a rule used without intermediate purification for feeding the subsequent stage. If necessary, additional inert gas and/or oxygen is metered in.

Examples of two-stage heterogeneously catalyzed gas-phase partial oxidations of at least one organic compound of molecular oxygen over fixed catalyst beds present in two fixed-bed reactors connected in series and containing a plurality of catalyst tubes are the gas-phase partial oxidation of propylene to acrylic acid (for which the claimed invention is described in more detail below by way of example) and the gas-phase partial oxidation of isobutene, methyl tert-butyl ether, tert-butanol and/or isobutyric acid to methacrylic acid.

In the first stage, the respective raw material is oxidized to acrolein or methacrolein and in the second stage the acrolein or methacrolein is oxidized to acrylic acid-or methacrylic acid. However, the context described for multistage heterogeneously catalyzed gas-phase partial oxidation also applies when the partial oxidation takes place in a plurality of successive steps and the totality of all steps is effected along a catalyst load housed in a single tube-bundle reactor, as described, for example, in DE-A 10121592 for the gas-phase partial oxidation of propylene to acrylic acid by way of example. An analogous procedure can also be adopted in the case of gas-phase partial oxidation of isobutene to methacrylic acid. There, it is entirely possible for the composition of the load to change along its length.

The propylene or isobutene, etc. used as a raw material are, as mentioned above, not pure starting materials but always contain certain amounts of impurities.

For example, a crude propylene having the two purities below, as isolated from crackers, is frequently used as propylene for the acrolein and/or acrylic acid preparation:

a) polymer-grade propylene:

| | |
|---|---|
| $\geq 99.6\%$ by weight | of propene, |
| $\leq 0.4\%$ by weight | of propane, |
| $\leq 300$ ppm by weight | of ethane and/or methane, |
| $\leq 5$ ppm by weight | of $C_4$-hydrocarbons, |
| $\leq 1$ ppm by weight | of acetylene, |
| $\leq 7$ ppm by weight | of ethylene, |
| $\leq 5$ ppm by weight | of water, |
| $\leq 2$ ppm by weight | of $O_2$, |
| $\leq 2$ ppm by weight | of sulfur-containing compounds (calculated as sulfur), |
| $\leq 1$ ppm by weight | of chlorine-containing compounds (calculated as chlorine), |
| $\leq 5$ ppm by weight | of CO, |
| $\leq 5$ ppm by weight | of $CO_2$, |
| $\leq 10$ ppm by weight | of cyclopropane, |
| $\leq 5$ ppm by weight | of propadiene and/or propyne, |
| $\leq 10$ ppm by weight | of $C_{\geq 5}$-hydrocarbon and |
| $\leq 10$ ppm by weight | of carbonyl-containing compounds (calculated as $Ni(CO)_4$); | b) chemical-grade propylene:

| | |
|---|---|
| $\geq 94\%$ by weight | of propene, |
| $\leq 6\%$ by weight | of propane, |
| $\leq 0.2\%$ by weight | of methane and/or ethane, |
| $\leq 5$ ppm by weight | of ethylene, |
| $\leq 1$ ppm by weight | of acetylene, |
| $\leq 20$ ppm by weight | of propadiene and/or propyne, |
| $\leq 100$ ppm by weight | of cyclopropane, |
| $\leq 50$ ppm by weight | of butene, |
| $\leq 50$ ppm by weight | of butadiene, |
| $\leq 200$ ppm by weight | of $C_4$-hydrocarbons, |
| $\leq 10$ ppm by weight | of $C_{\geq 5}$-hydrocarbons, |
| $\leq 2$ ppm by weight | of sulfur-containing compounds (calculated as sulfur), |
| $\leq 0.1$ ppm by weight | of sulfides (calculated as $H_2S$), |
| $\leq 1$ ppm by weight | of chlorine-containing compounds (calculated as chlorine), |
| $\leq 1$ ppm by weight | of chlorides (calculated as $Cl^-$) and |
| $\leq 30$ ppm by weight | of water. |

Of course, a mixture substantially comprising propene and propane, as described in WO 01/96270, can also be used as crude propylene.

For the first step, the heterogeneously catalyzed gas-phase partial oxidation of propylene to acrolein, all Mo-, Bi- and Fe-containing multimetal oxide materials are in principle suitable.

These are in particular the multimetal oxide active materials of the formula I of DE-A 19955176, the multimetal oxide active materials of the formula I of DE-A 19948523, the multimetal oxide active materials of the formula I of DE-A 19948523, the multimetal oxide active materials of the formulae I, II and III of DE-A 10101695, the multimetal oxide active materials of the formulae I, II and III of DE-A 19948248 and the multimetal oxide active materials of the formulae I, II and III of DE-A 19955168 and the multimetal oxide active materials mentioned in EP-A 700714.

The Mo-, Bi- and Fe-containing multimetal oxide catalysts which are disclosed in DE-A 10046957, DE-A 10063162, DE-C 3338380, DE-A 19902562, EP-A 15565, DE-C 2380765, EP-A 807465, EP-A 279374, DE-A 3300044, EP-A 575897, U.S. Pat. No. 4,438,217, DE-A 19855913, WO 98/24746, DE-A 19746210 (those of the formula II), JP-A 91/294239, EP-A 293224 and EP-A 700714 are furthermore suitable for this oxidation step. This applies in particular to the exemplary embodiments in these publications, among which those of EP-A 15565, EP-A 575897, DE-A 19746210 and DE-A 19855913 are particularly preferred. In this context, a catalyst according to example 1c of EP-A 15565 and a catalyst which is to be prepared in a corresponding manner but whose active material has the composition $Mo_{12}Ni_{6.5}Zn_2Fe_2Bi_1P_{0.0065}K_{0.06}O_x \cdot 10SiO_2$ are to be particularly singled out. Furthermore, the example with the consecutive number 3 in DE-A 19855913 (stoichiometry: $Mo_{12}Co_7Fe_3Bi_{0.6}K_{0.08}Si_{1.6}O_x$) as an unsupported catalyst in the form of hollow cylinders and measuring 5 mm×3 mm×2 mm (external diameter×height×internal diameter) and the unsupported catalyst comprising multimetal oxide II and according to example 1 of DE-A 19746210 are to be singled out. Further possible examples are the multimetal oxide catalysts of U.S. Pat. No. 4,438,217. The latter is applicable in particular when these hollow cylinders measure 5.5 mm×3 mm×3.5 mm or 5 mm×2 mm×2 mm or 5 mm×3 mm×2 mm or 6 mm×3 mm×3 mm or 7 mm×3 mm×4 mm (which is in each case external diameter×height×internal diameter).

A large number of the multimetal oxide active materials suitable for the step from propylene to acrolein can be subsumed under the formula I

$$Mo_{12}Bi_aFe_bX^1_cX^2_dX^3_eX^4_fO_n \quad (I),$$

where

X$^1$=nickel and/or cobalt,

X$^2$=thallium, an alkali metal and/or an alkaline earth metal,

X$^3$=zinc, phosphorus, arsenic, boron, antimony, tin, cerium, lead and/or tungsten, X$^4$=silicon, aluminum, titanium and/or zirconium, a=from 0.5 to 5, b=from 0.01 to 5, preferably from 2 to 4, c=from 0 to 10, preferably from 3 to 10, d=from 0 to 2, preferably from 0.02 to 2, e=from 0 to 8, preferably from 0 to 5, f=from 0 to 10 and n=is a number which is determined by the valency and frequency of the elements other than oxygen in I.

They are obtainable in a manner known per se (cf. for example DE-A 4023239) and are usually molded as such to give spheres, rings or cylinders or are used in the form of coated catalysts, i.e. premolded, inert supports coated with the active material. However, they can of course also be used in powder form as catalysts.

In principle, active materials of the formula I can be prepared in a simple manner by producing, from suitable sources of their elemental constituents, a very thorough, preferably finely divided dry mixture having a composition corresponding to their stoichiometry and calcining said mixture at from 350 to 650° C. The calcination can be effected either under inert gas or under an oxidizing atmosphere, e.g. air (mixture of inert gas and oxygen) or under a reducing atmosphere (e.g. a mixture of inert gas, NH$_3$, CO and/or H$_2$). The duration of calcination may be from a few minutes to a few hours and usually decreases with increasing temperature. Suitable sources of the elemental constituents of the multimetal oxide active materials I are those compounds which are already oxides and/or those compounds which can be converted into oxides by heating, at least in the presence of oxygen.

In addition to the oxides, in particular halides, nitrates, formates, oxalates, citrates, acetates, carbonate, amine complexes, ammonium salts and/or hydroxides are suitable as such starting compounds (compounds such as NH$_4$OH, (NH$_4$)$_2$CO$_3$, NH$_4$NO$_3$, NH$_4$CHO$_2$, CH$_3$COOH, NH$_4$CH$_3$CO$_2$ and/or ammonium oxalate, which decompose and/or can be decomposed at the latest during the subsequent calcination into compounds escaping in gaseous form, may additionally be incorporated into the thorough dry mixture).

The thorough mixing of the starting compounds for the preparation of multimetal oxide active materials I can be carried out in dry or in wet form. If it is effected in dry form, the starting compounds are expediently used in the form of a finely divided powder and, after the mixing and, if required, compaction, are subjected to calcination. However, the thorough mixing is preferably effected in wet form. Usually, the starting compounds are mixed with one another in the form of an aqueous solution and/or suspension. Particularly thorough dry mixtures are obtained in the mixing method described when exclusively those sources of the elemental constituents which are present in dissolved form are used as starting materials. A preferably used solvent is water. The aqueous material obtained is then dried, the drying process preferably being effected by spray-drying of the aqueous mixture at outlet temperatures of from 100 to 150° C.

The multimetal oxide active materials of the formula I can be used for the propene→acrolein step either in powder form or after molding to give specific catalyst geometries, it being possible to effect the shaping before or after the final calcination. For example, unsupported catalysts can be prepared from the powder form of the active material or its uncalcined and/or partially calcined precursor materials by compaction to give the desired catalyst geometry (for example by pelleting or extrusion), it being possible, if required, to add assistants, e.g. graphite or stearic acid as lubricants and/or molding assistants and reinforcing agents, such as microfibers of glass, asbestos, silicon carbide or potassium titanate. Suitable geometries for unsupported catalysts are, for example, solid cylinders or hollow cylinders having an external diameter and a length of from 2 to 10 mm. In the case of the hollow cylinder, a wall thickness of from 1 to 3 mm is expedient. The unsupported catalyst can of course also have spherical geometry, it being possible for the sphere diameter to be from 2 to 10 mm.

A particularly advantageous geometry for hollow cylinders is 5 mm×3 mm×2 mm (external diameter×length×internal diameter), particularly in the case of unsupported catalysts.

The shaping of the pulverulent active materials or of its pulverulent, still uncalcined and/or partially calcined precursor material can of course also be effected by application to premolded inert catalyst supports. The coating of the supports for the preparation of the coated catalysts is carried out as a rule in a suitable rotatable container, as disclosed, for example, in DE-A 2909671, EP-A 293859 or EP-A 714700. For coating of the supports, the powder material to be applied is expediently moistened and, after the application, is dried again, for example by means of hot air. The coat thickness of the powder material applied to the support is expediently chosen to be from 10 to 1 000 µm, preferably from 50 to 500 µm, particularly preferably from 150 to 250 µm.

Support materials which may be used are conventional porous or nonporous aluminas, silica, thorium dioxide, zirconium dioxide, silicon carbide or silicates, such as magnesium silicate or aluminum silicate. They are as a rule substantially inert with respect to the desired reaction on which the novel process is based. The supports may have a regular or irregular shape, regularly shaped supports having substantial surface roughness, for example spheres or hollow cylinders, being preferred. The use of substantially nonporous, spherical steatite supports which have a rough surface and whose diameter is from 1 to 8 mm, preferably from 4 to 5 mm, is suitable. However, it is also suitable to use as supports cylinders whose length is from 2 to mm and whose external diameter is from 4 to 10 mm. Where rings suitable according to the invention are used as supports, the wall thickness is moreover usually from 1 to 4 mm. Annular supports preferably to be used according to the invention have a length of from 2 to 6 mm, an external diameter of from 4 to 8 mm and a wall thickness of from 1 to 2 mm. According to the invention, rings measuring 7 mm×3 mm×4 mm (external diameter×length×internal diameter) are also particularly suitable as supports. The fineness of the catalytic active oxide materials to be applied to the surface of the support is of course adapted to the desired coat thickness (cf. EP-A 714 700).

Multimetal oxide active materials to be used for the step from propylene to acrolein are furthermore materials of the formula II

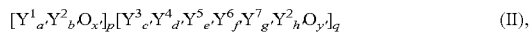  (II), where
Y$^1$=only bismuth or bismuth and at least one of the elements tellurium, antimony, tin and copper,
Y$^2$=molybdenum or molybdenum and tungsten,
Y$^3$=an alkali metal, thallium and/or samarium,
Y$^4$=an alkaline earth metal, nickel, cobalt, copper, manganese, zinc, tin, cadmium and/or mercury,
Y$^5$=iron or iron and at least one of the elements chromium and cerium,
Y$^6$=phosphorus, arsenic, boron and/or antimony,
Y$^7$=a rare earth metal, titanium, zirconium, niobium, tantalum, rhenium, ruthenium, rhodium, silver, gold, aluminum, gallium, indium, silicon, germanium, lead, thorium and/or uranium, a'=from 0.01 to 8,
b'=from 0.1 to 30,
c'=from 0 to 4,
d'=from 0 to 20,
e'=from 0 to 20,
f'=from 0 to 6,
g'=from 0 to 15,
h'=from 8 to 16,
x',y'=numbers which are determined by the valency and frequency of the elements other than oxygen in II and
p,q=numbers whose ratio p/q is from 0.1 to 10, comprising three-dimensional regions of the chemical composition $Y^1_{a'}Y^2_{b'}O_{x'}$ which are delimited from their local environment because of their composition differing from the local environment and whose maximum diameter (longest distance passing through the center of gravity of the region and connecting two points present on the surface (interface) of the region) is from 1 nm to 100 µm, frequently from 10 nm to 500 nm or from 1 µm to 50 or 25 µm.

Particularly advantageous novel multimetal oxide materials II are those in which Y$^1$ is only bismuth.

Preferred among these in turn are those which are of the formula III

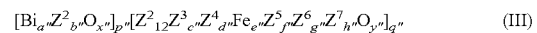  (III)

where
Z$^2$=molybdenum or molybdenum and tungsten,
Z$^3$=nickel and/or cobalt,
Z$^4$=thallium, an alkali metal and/or an alkaline earth metal,
Z$^5$=phosphorus, arsenic, boron, antimony, tin, cerium and/or lead,
Z$^6$=silicon, aluminum, titanium and/or zirconium,
Z$^7$=copper, silver and/or gold,
a''=from 0.1 to 1,
b''=from 0.2 to 2,
c''=from 3 to 10,
d''=from 0.02 to 2,
e''=from 0.01 to 5 preferably from 0.1 to 3,
f''=from 0 to 5,
g''=from 0 to 10,
h''=from 0 to 1,
x'',y''=numbers which are determined by the valency and frequency of the elements other than oxygen in III,
p'',q''=numbers whose ratio p''/q'' is from 0.1 to 5, preferably from 0.5 to 2, those materials III in which $Z^2_{b''}$ is (tungsten)$_{b''}$ and $Z^2_{12}$ is (molybdenum)$_{12}$ being very particularly preferred.

It is furthermore advantageous if at least 25 mol % (preferably at least 50, particularly preferably at least 100, mol %) of the total amount of $[Y^1_{a'}Y^2_{b'}O_{x'}]_p$ ($[Bi_{a''}Z^2_{b''}O_{x''}]_{p''}$) of the multimetal oxide materials II (multimetal oxide materials III) suitable according to the invention are present in the multimetal oxide materials II (multimetal oxide materials III) suitable according to the invention in the form of three-dimensional regions of the chemical composition $Y^1_{a'}Y^2_{b'}O_{x'}$, [$Bi_{a''}Z^2_{b''}O_{x''}$]) which are delimited from their local environment because of their chemical composition differing from the local environment and whose maximum diameter is from 1 nm to 100 µm.

Regarding the shaping, the statements made in the case of the catalysts comprising multimetal oxide materials I are applicable with regard to catalysts comprising multimetal oxide materials II.

The preparation of active materials of multimetal oxide materials II is described, for example, in EP-A 575897 and in DE-A 19855913.

The inert support materials recommended above are also suitable, inter alia, as inert materials for dilution and/or delimitation of the corresponding fixed catalyst beds or as a preliminary bed protecting them.

For the second step, the heterogeneously catalyzed gas-phase partial oxidation of acrolein to acrylic acid, all Mo- and V-containing multimetal oxide materials are in principle suitable as active materials, for example those of DE-A 10046928.

A large number thereof, for example those of DE-A 19815281, can be subsumed under the formula IV

$$Mo_{12}V_aX^1_bX^2_cX^3_dX^4_eX^5_fX^6_gO_n \qquad (IV),$$

where
- $X^1$=W, Nb, Ta, Cr and/or Ce,
- $X^2$=Cu, Ni, Co, Fe, Mn and/or Zn,
- $X^3$=Sb and/or Bi,
- $X^4$=one or more alkali metals,
- $X^5$=one or more alkaline earth metals,
- $X^6$=Si, Al, Ti and/or Zr,
- a=from 1 to 6,
- b=from 0.2 to 4,
- c=from 0.5 to 18,
- d=from 0 to 40,
- e=from 0 to 2,
- f=from 0 to 4,
- g=from 0 to 40 and
- n=a number which is determined by the valency and frequency of the elements other than oxygen in IV.

Those embodiments within the active multimetal oxides IV which are preferred according to the invention are those which are defined by the following meanings of the variables of the formula IV:
- $X^1$=W, Nb and/or Cr,
- $X^2$=Cu, Ni, Co and/or Fe,
- $X^3$=Sb,
- $X^4$=Na and/or K,
- $X^5$=Ca, Sr and/or Ba,
- $X^6$=Si, Al and/or Ti,
- a=from 1.5 to 5,
- b=from 0.5 to 2,
- c=from 0.5 to 3,
- d=from 0 to 2,
- e=from 0 to 0.2,
- f=from 0 to 1 and
- n=a number which is determined by the valency and frequency of the elements other than oxygen in IV.

However, multimetal oxides IV very particularly preferred according to the invention are those of the formula V

$$Mo_{12}V_{a'}Y^1_{b'}Y^2_{c'}Y^5_{f'}Y^6_{g'}O_{n'} \qquad (V)$$

where
- $Y^1$=w and/or Nb,
- $Y^2$=Cu and/or Ni,
- $Y^5$=Ca and/or Sr,
- $Y^6$=Si and/or Al,
- a'=from 2 to 4,
- b'=from 1 to 1.5,
- c'=from 1 to 3,
- f'=from 0 to 0.5,
- g'=from 0 to 8 and
- n'=a number which is determined by the valency and frequency of the elements other than oxygen in V.

The multimetal oxide active materials (IV) suitable according to the invention are obtainable in a manner known per se, for example that disclosed in DE-A 4335973 or in EP-A 714700.

Multimetal oxide active materials suitable for the step acrolein→acrylic acid, in particular those of the formula IV, can in principle be prepared in a simple manner by producing, from suitable sources of their elemental constituents, a very thorough, preferably finely divided dry mixture having a composition corresponding to their stoichiometry and calcining said mixture at from 350 to 600° C. The calcination can be carried out either under inert gas or under an oxidizing atmosphere, e.g. air (mixture of inert gas and oxygen) or under a reducing atmosphere (e.g. mixtures of inert gas and reducing gases, such as $H_2$, $NH_3$, CO, methane and/or acrolein or said reducing gases by themselves). The duration of calcination may be from a few minutes to a few hours and usually decreases with increasing temperature. Suitable sources of the elemental constituents of the multimetal oxide active materials IV are those compounds which are already oxides and/or those compounds which can be converted into oxides by heating, at least in the presence of oxygen.

The thorough mixing of the starting compounds for the preparation of multimetal oxide materials IV can be effected in dry or in wet form. If it is effected in dry form, the starting compounds are expediently used as finely divided powder and, after the mixing and, if required, compaction, are subjected to calcination. However, the thorough mixing is preferably effected in wet form.

The starting compounds are usually mixed with one another in the form of an aqueous solution and/or suspension. Particularly thorough dry mixtures are obtained in the mixing method described when exclusively those sources of the elemental constituents which are present in dissolved form are used as starting materials. The preferably used solvent is water. The aqueous material obtained is then dried, the drying process preferably being effected by spray-drying of the aqueous mixture at outlet temperatures of from 100 to 150° C.

The resulting multimetal oxide materials, in particular those of the formula IV, can be used for the acrolein oxidation either in powder form or after molding to give specific catalyst geometries, it being possible to effect the shaping before or after the final calcination. For example, unsupported catalysts can be prepared from the powder form of the active material or its uncalcined precursor material by compaction to give the desired catalyst geometry (for example by pelleting or extrusion), it being possible, if required, to add assistants, e.g. graphite or stearic acid as lubricants and/or molding assistants and reinforcing agents, such as microfibers of glass, asbestos, silicon carbide or potassium titanate. Suitable geometries for unsupported catalysts are, for example, solid cylinders or hollow cylinders having an external diameter and a length of from 2 to 10 mm. In the case of the hollow cylinders, a wall thickness of from 1 to 3 mm is expedient. Of course, the unsupported catalyst may also have spherical geometry, it being possible for the sphere diameter to be from 2 to 10 mm.

Of course, the shaping of the pulverulent active material or its pulverulent, still uncalcined, precursor material can also be effected by application to premolded inert catalyst supports. The coating of the supports for the preparation of the coated catalysts is as a rule carried out in a suitable rotatable container, as disclosed, for example, in DE-A 2909671, EP-A 293859 or EP-A 714700.

For coating the supports, the powder material to be applied is expediently moistened, and, after application, is dried again, for example by means of hot air. The coat thickness of the powder material applied to the support is expediently chosen to be from 10 to 1 000 µm, preferably from 50 to 500 µm, particularly preferably from 150 to 250 µm.

Support materials which may be used are conventional porous or nonporous aluminas, silica, thorium dioxide, zirconium dioxide, silicon carbide or silicates, such as magnesium silicate or aluminum silicate. The supports may have a regular or irregular shape, regularly shaped supports having substantial surface roughness, for example spheres or hollow cylinders covered in chips, being preferred. The use of substantially nonporous, spherical steatite supports which have a rough surface and whose diameter is from 1 to 8 mm, preferably from 4 to 5 mm, is suitable. However, it is also suitable to use as supports cylinders whose length is from 2 to 10 mm and whose external diameter is from 4 to 10 mm. Where rings are used as supports, the wall thickness is moreover usually from 1 to 4 mm. Annular supports to be preferably used have a length of from 2 to 6 mm, an external diameter of from 4 to 8 mm and a wall thickness of from 1 to 2 mm. Rings measuring 7 mm×3 mm×4 mm (external diameter×length×internal diameter) are also particularly suitable as supports. The fineness of the catalytically active oxide materials to be applied to the surface of the support is of course adapted to the desired coat thickness (cf. EP-A 714 700).

Advantageous multimetal oxide active materials to be used for the acrolein→acrylic acid step are furthermore materials of the formula VI $$[D]_p[E]_q \quad (VI),$$

where $D=Mo_{12}V_{a''}Z^1_{b''}Z^2_{c''}Z^3_{d''}Z^4_{e''}Z^5_{f''}Z^6_{g''}O_{x'''}$,
$E=Z^7_{12}Cu_{h''}H_{i''}O_{y''}$,
$Z^1$=W, Nb, Ta, Cr and/or Ce,
$Z^2$=Cu, Ni, Co, Fe, Mn and/or Zn,
$Z^3$=Sb and/or Bi,
$Z^4$=Li, Na, K, Rb, Cs and/or H
$Z^5$=Mg, Ca, Sr and/or Ba,
$Z^6$=Si, Al, Ti and/or Zr,
$Z^7$=Mo, W, V, Nb and/or Ta, preferably Mo and/or W
a''=from 1 to 8,
b''=from 0.2 to 5,
c''=from 0 to 23,
d''f=from 0 to 50,
e''=from 0 to 2,
f''=from 0 to 5,
g''=from 0 to 50,
h''=from 4 to 30,
i''=from 0 to 20 and
x'',y''=numbers which are determined by the valency and frequency of the elements other than oxygen in VI and
p,q=numbers which differ from zero and whose ratio p/q is 160:1 to 1:1, which are obtainable by separately preforming a multimetal oxide material E $$Z^7_{12}Cu_{h''}H_{i''}O_{y''} \quad (E),$$

in finely divided form (starting material 1) and then incorporating the preformed solid starting material 1 into an aqueous solution, an aqueous suspension or a finely divided dry mixture of sources of the elements Mo, V, $Z^1$, $Z^2$, $Z^3$, $Z^4$, $Z^5$, $Z^6$, which contains the abovementioned elements in the stoichiometry D $$Mo_{12}V_{a''}Z^1_{b''}Z^2_{c''}Z^3_{d''}Z^4_{e''}Z^5_{f''}Z^6_{g''} \quad (D),$$

(starting material 2), in the desired ratio p:q, drying the possibly resulting aqueous mixture, and calcining the dry precursor material thus obtained, before or after its drying to give the desired catalyst geometry, at from 250 to 600° C.

The multimetal oxide materials VI, in which the incorporation of the preformed solid starting material 1 in an aqueous starting material 2 is effected at ≦70° C., are preferred. A detailed description of the preparation of catalysts comprising multimetal oxide materials VI is contained, for example, in EP-A 668104, DE-A 19736105, DE-A 10046928, DE-A 19740493 and DE-A 19528646.

Regarding the shaping, the statements made in the case of the catalysts comprising multimetal oxide materials IV are applicable with regard to catalysts comprising multimetal oxide materials VI.

Multimetal oxide catalysts outstandingly suitable for the acrolein→acrylic acid step are also those of DE-A 19815281, in particular comprising multimetal oxide active materials of the formula I of this document.

Unsupported catalyst rings are advantageously used for the step from propylene to acrolein, and coated catalyst rings for the step from acrolein to acrylic acid.

The first step, from propylene to acrolein, can be carried out using the catalysts described, for example in a one-zone fixed-bed reactor having a plurality of catalyst tubes, as described by DE-A 4431957.

The oxidizing agent used is oxygen. If $N_2$ is chosen as inert diluent gas, the use of air as an oxygen source proves particularly advantageous.

As a rule, the volume (l(S.T.P.)) ratio of propane to oxygen to inert gases (including steam) is 1:(1.0 to 3.0):(5 to 25), preferably 1:(1.7 to 2.3):(10 to 15). The reaction pressure is usually from 1 to 3 bar and the total space velocity is preferably from 1500 to 2900 l(S.T.P.) per l per h. The propene loading is typically from 90 to 160 l(S.T.P.) per l per h or even up to 200 l(S.T.P.) per l per h and more.

The one-zone fixed-bed reactor having a plurality of catalyst tubes is preferably fed from above with the feed gas mixture. An expediently used heat exchange medium is a salt melt, preferably consisting of 60% by weight of potassium nitrate ($KNO_3$) and 40% by weight of sodium nitrite ($NaNO_2$).

Considered over the reactor, salt melt and reaction gas mixture may be passed either cocurrent or countercurrent. The salt melt itself is preferably passed in a meandering manner around the catalyst tubes.

If the flow approaches the catalyst tubes in a downward direction, it is expedient to load the catalyst tubes as follows from bottom to top (if the flow were to approach in an upward direction, the loading sequence would expediently be reversed):

first, over a length of from 40 to 60% of the catalyst tube length, either only catalyst or a mixture of catalyst and inert material, the latter accounting for up to 20% by weight, based on the mixture (section C);

then, over a length of from 20 to 40% of the total tube length, either only catalyst or a mixture of catalyst and inert material, the latter accounting for up to 40% by weight, based on the mixture (section,B); and finally, over a length of from 10 to 20% of the total tube length, a bed of inert material (section A).

Section C is preferably undiluted.

The abovementioned loading variant is expedient particularly when catalysts used are those according to example 1 of DE-A 10046957 or according to example 3 of DE-A 10046957 and inert material used comprises steatite rings measuring 7 mm×7 mm×4 mm (external diameter×height× internal diameter). Regarding the salt bath temperature, the statements made in DE-A 4431957 are applicable.

The first step, from propylene to acrolein, can be carried out using the catalysts described but also, for example, in a two-zone fixed-bed reactor having a plurality of catalyst tubes, as described in DE-A 19910506. In both cases described above, the propene conversion achieved in a single pass is usually ≧90 mol % or ≧95 mol %. The second step, from acrolein to acrylic acid, can be carried out using the catalysts described, for example in a one-zone fixed-bed reactor having a plurality of catalyst tubes, as described in DE-A 4431949.

It is possible to start from crude acrolein for producing the feed gas mixture. However, it is particularly advantageous to use the acrolein-containing product gas mixture of a first stage based on the first step (as described above) for feeding (if appropriate after intermediate cooling thereof). The oxygen required for the second step is preferably added in the form of air and, in the second case, is added directly to the product gas mixture.

As a rule, the feed gas mixture of such a second stage then has the following composition: acrolein:oxygen:steam:inert gas volume ratio (l(S.T.P.)) of 1:(1 to 3):(0 to 20):(3 to 30), preferably of 1:(1 to 3):(0.5 to 10):(7 to 18).

Here too, the reaction pressure is as a rule from 1 to 3 bar and the total space velocity is preferably from 1000 to 2500 l(S.T.P.) per l per h. The acrolein space velocity is typically from 80 to 150 l(S.T.P) per l per h or even up to 180 l(S.T.P.) per l per h and more.

Preferably, the feed gas mixture likewise flows from above toward the one-zone fixed-bed reactor having a plurality of catalyst tubes. In the second stage too, the heat exchange medium used is expediently a salt melt, preferably consisting of 60% by weight of potassium nitrate ($KNO_3$) and 40% by weight of sodium nitrite ($NaNO_2$). Considered over the reactor, salt melt and reaction gas mixture may be passed either cocurrent or countercurrent. The salt melt itself is preferably passed in a meandering manner into the catalyst tubes.

If the flow to the catalyst tubes is in an downward direction, it is expedient to load the catalyst tubes as follows from bottom to top:

first, over a length of from 50 to 70% of the catalyst tube length, either only catalyst or a mixture of catalyst and inert material, the latter accounting for up to 20% by weight, based on the mixture (section C);

then, over a length of from 20 to 40% of the total tube length, either only catalyst or a mixture of catalyst and inert material, the latter accounting for up to 40% by weight, based on the mixture (section B); and finally, over a length of from 5 to 20% of the total tube length, a bed of inert material (section A).

Section C is preferably undiluted.

The abovementioned loading variant is expedient particularly when the catalysts used are those according to preparation example 5 of DE-A 10046928 or those according to DE-A 19815281 and steatite rings measuring 7 mm×7 mm×4 mm or 7 mm×7 mm×3 mm (in each case external diameter×height×internal diameter) are used as inert material. Regarding the salt bath temperature, the statements made in DE-A 44 319 49 are applicable. It is chosen as a rule so that the acrolein conversion achieved in a single pass is usually ≧90 mol % or ≧95 mol %.

The second step, from acrolein to acrylic acid can be carried out using the catalysts described but also, for example, in a two-zone fixed-bed reactor having a plurality of catalyst tubes, as described in DE-19910508. The abovementioned is applicable with regard to the acrolein conversion. When the second step is carried out in a two-zone fixed-bed reactor having a plurality of catalyst tubes, it is also possible to start from crude acrolein for producing the feed gas mixture or directly to use the product gas mixture of a first stage based on the first step (if required after intermediate cooling thereof) (as described above). The oxygen required for the second step is preferably added in the form of air and, in the second case, is added directly to the product gas mixture.

In a two-stage procedure with direct further use of the product gas mixture of the first stage for feeding the second stage, as a rule two one-zone fixed-bed reactors having a plurality of catalyst tubes or two two-zone fixed-bed reactors having a plurality of catalyst tubes are connected in series. A mixed series (one-zone/two-zone or vice versa) is also possible.

An intermediate condenser which may contain inert beds which can perform a filter function may be present between the reactors.

The salt bath temperature of reactors having a plurality of catalyst tubes for the first stage is as a rule from 300 to 400° C. The salt bath temperature of said reactors for the second stage is generally from 200 to 350° C.

What is important for the invention is that, for all abovementioned configurations, the novel process can be used in each case for both stages, both when the two stages are operated independently of one another and when, as described above, they are operated connected in series. However, it is also successful when both steps are carried out, as described in DE-A 10121592, in a reactor over one load.

In all cases, the partial catalyst change may extend to up to 80% or only up to 70% or only up to 60% or only up to 50% or only up to 40% or only up to 30% or preferably up to 25%, particularly preferably from 30 to 50%, very particularly preferably from 35 to 45%, of the bed length of the fixed catalyst bed, in the direction of flow (a top load consisting of 100% of inert material (the first load in the direction of flow) is not considered to belong to the fixed catalyst bed; for reasons of expediency, this top load would, however, also be replaced; in a corresponding manner, a final load consisting of 100% of inert material (the end load in the direction of flow) would also not e considered to belong to the fixed catalyst bed; an intermediate load consisting of 100% of inert material would, however, be considered to belong to the fixed catalyst bed).

Expediently, the abovementioned percentage for partial catalyst change is frequently not less than 10% or 20%.

Finally, it should be mentioned that a part of the feed gas mixture of the first stage (propene-acrolein) may be recycle gas. This is gas which remains after isolation of the product (acrylic acid isolation) from the product gas mixture of the second stage and, when the two stages are connected in series, is as a rule partly recycled as inert diluent gas for feeding the first and/or second stage.

A typical recycle gas composition is:

0–0.1% by volume of others, e.g. biphenyl, diphenyl ether and/or dimenthyl phthalate, 0–0.1% by volume of acrylic acid,
0–0.1% by volume of acrolein,
3–5% by volume of oxygen,
1–5% by volume of steam,
0–3% by volume of carbon monoxide,
0–8% by volume of carbon dioxide,
0–2% by volume of propane,
0.1–0.5% by volume of propylene,
85–95% by volume of nitrogen.

The acrylic acid can be isolated as described in EP-A 982 287, EP-A 982 289, DE-A 19924532, DE-A 10115277, DE-A 19606877, DE-A 19740252, DE-A 19627847, DE-A 10053086, EP-A 982 288 and DE-A 19627847.

Finally, it should be noted that, particularly when carrying out two successive oxidation steps in only one fixed-bed reactor having a plurality of catalyst tubes, it may be advantageous to carry out the partial catalyst change with the abovementioned percentages beginning from the outlet of the product gas mixture toward the inlet of the reaction gas mixture. In these cases, it is expedient to feed the reactor with reaction gas starting mixture from below, i.e. the load fraction intended for the partial change expediently forms the end of the catalyst tube load (considered from bottom to top).

In principle, the partial catalyst change can be carried out at any time, i.e. for example after an operating time of one year, two years, three years or several years. As a rule, it is carried out according to cost-efficiency considerations.

Finally, it may be mentioned that the novel partial catalyst change generally also has an advantageous effect on the pressure drop during the passage of the reaction mixture through the catalyst load.

Moreover, the heat exchange media (salt melts) are usually passed through the relevant fixed-bed reactors having a plurality of catalyst tubes in amounts such that the difference between their inlet temperature and their outlet temperature is as a rule <5° C.

EXAMPLES

A) Process for the two-stage heterogeneously catalyzed gas-phase partial oxidation of propylene to acrylic acid in two one-zone fixed-bed reactors having a plurality of catalyst tubes and connected in series I. Description of the general process conditions in the first stage

| | |
|---|---|
| Heat exchange medium used: | Salt melt consisting of 60% by weight of potassium nitrate and 40% by weight of sodium nitrite. |
| Material of the catalyst tubes: | ferritic steel. |
| Dimensions of the catalyst tubes: | 3 200 mm length; 25 mm internal diameter; 30 mm external diameter (wall thickness: 2.5 mm). |
| Number of catalyst tubes in the tube bundle: | 25 500. |
| Reactor: | Cylindrical container having a diameter of 6 800 mm; tube bundle arranged in an annular manner and having a free central space. |
| Diameter of the central free space: | 1 000 mm. Distance from the catalyst tubes located furthest outward to the container wall: 150 mm. Homogeneous catalyst tube distribution in the tube bundle (6 equidistant adjacent tubes per catalyst tube). |
| Catalyst tube spacing: | 38 mm. The catalyst tubes were fastened with a seal with their ends in catalyst tube sheets having a thickness of 125 mm and opened with their orifices into one hood each connected at the upper and lower end to the container. |
| Feed of the heat exchange medium to the tube bundle: | The tube bundle was divided into four equidistant (730 mm each) longitudinal sections (zones) by three baffle plates (each 10 mm thick) mounted in succession between the catalyst tube sheets along said catalyst tubes. |

The lowermost and the uppermost baffle plates had an annular geometry, the internal ring diameter being 1000 mm and the external ring diameter extending to the container wall and being sealed therein. The catalyst tubes were not fastened with a seal to the baffle plates. Rather, a <0.5 mm wide gap was left so that the transverse flow velocity of the salt melt inside a zone was very constant.

The middle baffle plate was circular and extended up to the catalyst tubes of the tube bundle which were located furthest outside.

The salt melt was circulated by means of two salt pumps, each of which supplied a longitudinal half of the tube bundle.

The pumps forced the salt melt into an annular channel which was mounted below the reactor jacket and distributed the salt melt over the container circumference. The salt melt passed through windows present in the reactor jacket to the tube bundle in the lowermost longitudinal section. Depending on the baffle plates, the salt melt then flowed in the following sequence from the outside to the inside,
from the inside to the outside,
from the outside to the inside,
from the inside to the outside, substantially in a meandering manner, considered over the container, from bottom to top. Through windows located in the uppermost longitudinal section around the container circumference, the salt melt collected in an upper annular channel mounted around the reactor jacket and, after cooling to the original inlet temperature, was forced by the pumps back into the lower annular channel.

| | |
|---|---|
| Composition of the reaction gas starting mixture (mixture of air, polymer-grade propylene and recycle gas): | 5.4% by volume of propene, 10.5% by volume of oxygen, 1.2% by volume of $CO_x$, 81.3% by volume of $N_2$, 1.6% by volume of $H_2O$. |
| Reactor loading: | Salt melt and reaction gas mixture were passed countercurrently, considered over the reactor. The salt melt entered at the bottom and the reaction gas mixture at the top. The inlet temperature of the salt melt was initially 337° C. The outlet temperature of the salt melt was 339° C. The pump delivery was 6 200 m³ of salt melt per hour. The reaction gas starting mixture was fed to the reactor at 300° C. |
| Loading with reaction gas starting mixture: | 68 845 m³ (S.T.P.)/h. |
| Propene loading of the catalyst load: | 110 h⁻¹. |

| Catalyst tube loading | Zone A: 50 cm |
|---|---|
| (from top to bottom): | preliminary bed of steatite rings measuring 7 mm × 7 mm × 4 mm (external diameter × length × internal diameter) |
| | Zone B: 100 cm |
| | catalyst load comprising a homogeneous mixture of 30% by weight of steatite rings measuring 5 mm × 3 mm × 2 mm (external diameter × length × internal diameter) and 70% by weight of unsupported catalyst from zone C). |
| | Zone C: 170 cm |
| | catalyst load comprising annular (5 mm × 3 mm × 2 mm = external diameter × length × internal diameter) unsupported catalyst according to example 1 of DE-A 10046957. |

II. Description of the intermediate cooling

The product gas mixture leaving the first reaction stage at 339° C. was passed, for intermediate cooling, through a one-zone tube-bundle heat exchanger which was cooled with a salt melt comprising 60% by weight of potassium nitrate and 40% by weight of sodium nitrite, made of ferritic steel and flanged directly to the reactor. The distance from the lower tube sheet of the reactor to the upper tube sheet of the condenser was 10 cm. The salt melt and the product gas mixture was fed countercurrently, considered over the heat exchanger. The salt bath itself flowed in a meandering manner in the same way as in the one-zone fixed-bed reactor having a plurality of catalyst tubes, around the cooling tubes through which the product gas mixture was passed. The length of the cooling tubes was 1.65 m, the internal diameter was 2.6 cm and the wall thickness was 2.5 mm. The number of cooling tubes was 8000. The diameter of the heat exchanger was 7.2 m.

They were distributed uniformly over the cross section, with uniform tube spacing.

Stainless steel spirals whose cross section virtually corresponded to that of the cooling tubes were introduced into the entrance of the cooling tubes (in the direction of flow). They served for improving the heat transfer.

The product gas mixture left the intermediate condenser at 250° C. Compressed air which was at 140° C. was then mixed in an amount of 6692 m³(S.T.P.)/h with said product gas mixture.

The feed gas mixture obtained was fed at 220° C. to the one-zone fixed-bed reactor of the second stage, which reactor had a plurality of catalyst tubes.

III. Description of the general process conditions in the second stage

A one-zone fixed-bed reactor having a plurality of catalyst tubes was used, said reactor being of the same design as that of the first stage.

Salt melt and reaction gas mixture were passed countercurrently, considered over the reactor. The salt melt entered at the bottom and the reaction gas mixture at the top.

The inlet temperature of the salt melt was initially 265° C. The outlet temperature of the salt melt was 267° C. The pump delivery was 6200 m³ of salt melt per hour.

The loading with feed gas mixture was 75537 m³(S.T.P.)/h.

| The catalyst tube loading | Zone A: |
|---|---|
| (from top to bottom) was: | 20 cm preliminary bed of steatite rings measuring 7 mm × 7 mm × 4 mm (external diameter × length × internal diameter). |
| | Zone B: |
| | 100 cm catalyst load comprising a homogeneous mixture of 30% by weight of steatite rings measuring 7 mm × 3 mm × 4 mm (external diameter × length × internal diameter) and 70% by weight of coated catalyst from zone C. |
| | Zone C: |
| | 200 cm catalyst load comprising annular (about 7 mm × 3 mm × 4 mm) coated catalyst according to preparation example 5 of DE-A 10046928. |

The analysis of the product gas mixture of the second stage gave the following results:

The conversion of the acrolein formed in the first stage, with freshly formed catalyst load of the second stage, at a salt melt inlet temperature of 265° C. in the second stage, was 99.3 mol % at a selectivity of 88.9 mol % for the acrylic acid formation (these data, like the data below, are always based on a single pass).

The acrolein conversion in the second stage decreased with increasing duration of operation.

By gradually increasing the temperature of the salt melt on entry into the second stage, it was possible to compensate this loss of activity.

After operation for several years under otherwise identical conditions, the salt melt inlet temperature required for this purpose in the second stage was 290° C. The selectivity of the acrylic acid formation simultaneously decreased to 87.5 mol %.

Removal of zone A and of 30 cm of zone B by suction and replacement thereof by a corresponding fresh load in the second stage led to the original acrolein conversion at a salt melt inlet temperature in the second stage of only 287° C., at a selectivity of 87.9 mol % for the acrylic acid formation.

Removal of zone A and of 60 cm of zone B by suction and replacement thereof by a corresponding fresh load in the second stage led to the original acrolein conversion at a salt melt inlet temperature in the second stage of only 281° C., at a selectivity of 88.3 mol % for the acrylic acid formation.

Removal of zone A, of zone B and of 20 cm of zone C by suction and replacement thereof by a corresponding fresh load in the second stage led to the original acrolein conversion at a salt melt inlet temperature in the second stage of only 270° C., at a selectivity of 88.9 mol % for the acrylic acid formation.

Removal of zone A, of zone B and of 50 cm of zone C by suction and replacement thereof by a corresponding fresh load in the second stage led to the original acrolein conversion at a salt melt inlet temperature in the second stage of only 267° C., at a selectivity of 88.9 mol % for the acrylic acid formation.

This means that replacement of less than 50% of the catalyst active material of the second stage led to virtually 100% restoration of activity and selectivity of the catalyst load of the second stage.

The isolation of the acrylic acid and the recycle gas formation were carried out as described in WO 97/48669.

B) The abovementioned Example A) leads qualitatively to the same result if, instead of the one-zone fixed-bed reactors having a plurality of catalyst tubes, the two-zone fixed-bed reactors having a plurality of catalyst tubes and according to DE-A 19910506 and DE-A 19910508 and the process conditions stated in these documents are used.

C) Both in example A) and in example B), the catalyst according to example 3 of DE-A 10046957 can also be used as catalyst for the first stage, and a catalyst according to DE-A 19815281 as a two-stage catalyst. The volume-specific activity profile is retained.

We claim:

1. A process for the heterogeneously catalyzed gas-phase partial oxidation of at least one organic compound with molecular oxygen over a fixed catalyst bed present in a fixed-bed reactor containing a plurality of catalyst tubes, in which there is an increasing reduction of the quality of the catalyst load with increasing duration of operation from a specific operating time, wherein, in order to recover the quality of the catalyst load, only a portion of spent catalyst load, instead of the entire spent catalyst load, is removed from the fixed-bed reactor containing a plurality of catalyst tubes and is replaced by a fresh catalyst load.

2. A process as claimed in claim 1, wherein the gas-phase partial oxidation is that of propylene to acrolein and/or acrylic acid or that of isobutene to methacrolein and/or methacrylic acid or that of acrolein to acrylic acid or that of methacrolein to methacrylic acid or that of propane to acrylic acid or that of isobutane to methacrylic acid.

3. A process as claimed in claim 1, wherein the catalyst load comprises Mo-, Bi- and Fe- and/or Mo- and V-containing multimetal oxide active materials.

4. A process as claimed in claim 1, wherein the gas-phase partial oxidation is the second stage of a two-stage gas-phase partial oxidation.

5. A process as claimed in claim 4, wherein the gas-phase partial oxidation is the partial oxidation of acrolein to acrylic acid in a two-stage gas-phase partial oxidation of propylene to acrylic acid.

6. A process as claimed in claim 5, wherein the catalyst load is a multimetal oxide material of the formula IV

$$Mo_{12}V_aX^1_bX^2_cX^3_dX^4_eX^5_fX^6_gO_n \qquad (IV),$$

where
X$^1$=W, Nb, Ta, Cr and/or Ce,
X$^2$=Cu, Ni, Co, Fe, Mn and/or Zn,
X$^3$=Sb and/or Bi,
X$^4$=one or more alkali metals,
X$^5$=one or more alkaline earth metals,
X$^6$=Si, Al, Ti and/or Zr,
a=from 1 to 6,
b=from 0.2 to 4,
c=from 0.5 to 18,
d=from 0 to 40,
e=from 0 to 2,
f=from 0 to 4,
g=from 0 to 40 and
n=a number which is determined by the valency and frequency of the elements other than oxygen in IV.

7. A process as claimed in claim 6, wherein the fixed-bed reactor containing a plurality of catalyst tubes is a one-zone or a two-zone fixed-bed reactor containing a plurality of catalyst tubes.

8. A process as claimed in claim 4, wherein the catalyst load of the first stage comprises an Mo-, Bi- and Fe-containing multimetal oxide and the fixed-bed reactor containing a plurality of catalyst tubes and used for the first stage is a one-zone or two-zone fixed-bed reactor containing a plurality of catalyst tubes.

9. A process as claimed in claim 4, wherein the product gas mixture of the first stage is used as such for feeding the second stage.

10. A process as claimed in claim 1, wherein the portion removed extends to up to 80% of the length of the fixed catalyst bed.

11. A process as claimed in claim 1, wherein the volume-specific activity of the catalyst load in the direction of flow of the reaction gas mixture increases continuously or stepwise.

12. A process as claimed in claim 1, wherein the gas-phase partial oxidation is that of propylene to acrolein and/or acrylic acid.

13. A process as claimed in claim 1, wherein the gas-phase partial oxidation is that of isobutene to methacrolein and/or methacrylic acid.

14. A process as claimed in claim 1, wherein the gas-phase partial oxidation is that of acrolein to acrylic acid.

15. A process as claimed in claim 1, wherein the gas-phase partial oxidation is that of methacrolein to methacrylic acid.

16. A process as claimed in claim 1, wherein the gas-phase partial oxidation is that of propane to acrylic acid.

17. A process as claimed in claim 1, wherein the gas-phase partial oxidation is that of isobutane to methacrylic acid.

18. A process as claimed in claim 1, wherein the portion of spent catalyst load removed is 10% or more of the length of the fixed catalyst bed.

19. A process as claimed in claim 18, wherein the portion of spent catalyst load removed extends up to 80% of the length of the fixed catalyst bed.

20. A process as claimed in claim 18, wherein the portion of spent catalyst load removed extends up to 70% of the length of the fixed catalyst bed.

21. A process as claimed in claim 18, wherein the portion of spent catalyst load removed extends up to 60% of the length of the fixed catalyst bed.

22. A process as claimed in claim 18, wherein the portion of spent catalyst load removed extends up to 50% of the length of the fixed catalyst bed.

23. A process as claimed in claim 18, wherein the portion of spent catalyst load removed extends up to 40% of the length of the fixed catalyst bed.

24. A process as claimed in claim 18, wherein the portion of spent catalyst load removed extends up to 30% of the length of the fixed catalyst bed.

25. A process as claimed in claim 18, wherein the portion of spent catalyst load removed extends up to 25% of the length of the fixed catalyst bed.

26. A process as claimed in claim 1, wherein the portion of spent catalyst load removed is 20% or more of the length of the fixed catalyst bed.

27. A process as claimed in claim 26, wherein the portion of spent catalyst load removed extends up to 80% of the length of the fixed catalyst bed.

28. A process as claimed in claim 26, wherein the portion of spent catalyst load removed extends up to 70% of the length of the fixed catalyst bed.

29. A process as claimed in claim 26, wherein the portion of spent catalyst load removed extends up to 60% of the length of the fixed catalyst bed.

30. A process as claimed in claim 26, wherein the portion of spent catalyst load removed extends up to 50% of the length of the fixed catalyst bed.

31. A process as claimed in claim 26, wherein the portion of spent catalyst load removed extends up to 40% of the length of the fixed catalyst bed.

32. A process as claimed in claim 26, wherein the portion of spent catalyst load removed extends up to 30% of the length of the fixed catalyst bed.

33. A process as claimed in claim 26, wherein the portion of spent catalyst load removed extends up to 25% of the length of the fixed catalyst bed.

34. A process as claimed in claim 1, wherein the portion of spent catalyst load removed ranges from 30 to 50% of the length of the fixed catalyst bed.

35. A process as claimed in claim 1, wherein the portion of spent catalyst load removed ranges from 35 to 45% of the length of the fixed catalyst bed.

36. A process as claimed in claim 12, wherein the portion of spent catalyst load removed is 10% or more of the length of the fixed catalyst bed.

37. A process as claimed in claim 12, wherein the portion of spent catalyst load removed is 20% or more of the length of the fixed catalyst bed.

38. A process as claimed in claim 14, wherein the portion of spent catalyst load removed is 10% or more of the length of the fixed catalyst bed.

39. A process as claimed in claim 14, wherein the portion of spent catalyst load removed is 20% or more of the length of the fixed catalyst bed.

* * * * *